United States Patent [19]

Barthomeuf et al.

[11] Patent Number: 4,554,398

[45] Date of Patent: Nov. 19, 1985

[54] PROCESS FOR THE SEPARATION OF $C_9$ AROMATIC ISOMERS

[75] Inventors: Denise M. Barthomeuf, Lyons, France; Daniel D. Rosenfeld, Houston, Tex.

[73] Assignee: Exxon Research & Engineering Co., Florham Park, N.J.

[21] Appl. No.: 665,466

[22] Filed: Oct. 29, 1984

[51] Int. Cl.[4] ............... C07C 7/13; C10G 25/03
[52] U.S. Cl. .................. 585/828; 208/310 Z
[58] Field of Search ............ 585/828; 208/310 Z

[56] References Cited

U.S. PATENT DOCUMENTS

| | | | |
|---|---|---|---|
| 3,308,069 | 3/1967 | Wadlinger et al. | 502/62 |
| 3,686,342 | 8/1972 | Neuzil | 208/310 Z X |
| 3,793,385 | 2/1974 | Bond et al. | 208/310 Z |
| 3,864,416 | 2/1975 | Campbell et al. | 208/310 Z X |
| 3,894,109 | 7/1975 | Rosback | 208/310 Z X |

FOREIGN PATENT DOCUMENTS

| | | | |
|---|---|---|---|
| 0037129 | 11/1979 | Japan | 585/828 |
| 1330956 | 9/1973 | United Kingdom | 585/828 |

*Primary Examiner*—D. E. Gantz
*Assistant Examiner*—Glenn A. Caldarola
*Attorney, Agent, or Firm*—M. D. Bittman

[57] ABSTRACT

A process for separating a $C_9$ aromatic isomer from a feed stream containing a mixture of $C_9$ aromatic isomers by contacting the feed stream with a bed of the adsorbent zeolite beta. The adsorbed $C_9$ aromatic isomer is removed from the adsorbent by desorption.

31 Claims, No Drawings

PROCESS FOR THE SEPARATION OF C$_9$ AROMATIC ISOMERS

BACKGROUND OF THE INVENTION

The field of art to which the claimed invention pertains is hydrocarbon separation. More specifically, the claimed invention relates to the separation of a C$_9$ aromatic isomer from a hydrocarbon feedstream containing a mixture of C$_9$ aromatic isomers by use of the adsorbent zeolite beta which selectively removes a C$_9$ aromatic isomer from the feed stream. The selectively adsorbed C$_9$ aromatic isomer is removed from the adsorbent through a desorption step.

DESCRIPTION OF THE PRIOR ART

It is known in the separation art that certain adsorbents generally comprising crystalline aluminosilicates can be utilized to separate certain hydrocarbons from mixtures thereof. In the separation of aromatic hydrocarbon isomers with certain crystalline aluminosilicates containing selected cations at the zeolitic cationic sites selectivity of the zeolite for a given aromatic isomer is enhanced. This manner of separation is particularly useful when the components to be separated have similar physical properties, such as freezing and boiling points which renders the components difficult to separate by distillation or crystallization.

A number of processes describing the separation of paraxylene from a mixture of at least one other xylene isomer utilizing a crystalline aluminosilicate adsorbent, are shown in U.S. Pat. Nos. 3,558,730, 3,558,732, 3,626,020, and 3,663,638. Other processes which describe the adsorption separation of the ethylbenzene from a mixture of xylene isomers utilizing a crystalline aluminosilicate adsorbent are shown in U.S. Pat. Nos. 3,943,182, 3,997,619, 3,998,901, and 4,021,499.

U.S. Pat. No. 3,793,385 discloses the use of the crystalline aluminosilicate zeolite beta to separate C$_8$ aromatic isomers, specifically to separate p-xylene and ethylbenzene from a mixture containing at least one other C$_8$ aromatic isomer. While the use of various zeolites to separate C$_8$ aromatic isomers is known, less is known about adsorbents which effectively separate the C$_9$ aromatic isomers.

The C$_9$ aromatic isomers are useful in the chemical arts as desorbents in separation processes and as precursors in preparing other chemicals. More specifically para-ethyltoluene is used in preparing plastics, pseudocumene which is used in the manufacture of dyes, plasticizers and pharmaceuticals and mesitylene as a precursor for high temperature resins. However, the availability of these C$_9$ aromatic isomers is restricted due to the difficulty of effectively separating a C$_9$ aromatic isomer from a mixture of the C$_9$ aromatic isomers.

SUMMARY OF THE INVENTION

It is accordingly a broad objective of this invention to provide a process of separating a C$_9$ aromatic isomer from a hydrocarbon feed stream containing a mixture of C$_9$ aromatic isomers.

In brief, the invention comprises an adsorptive separation process for the separation of the C$_9$ aromatic isomers from a hydrocarbon feed stream containing a mixture of C$_9$ aromatic isomers by contacting the hydrocarbon feed stream with a bed of the adsorbent zeolite beta. A raffinate stream is then withdrawn from the bed, this stream containing less of the selectively adsorbed C$_9$ aromatic isomer. The adsorbed C$_9$ aromatic isomer on the bed is then desorbed to effect displacement of the isomer, followed by withdrawing from the adsorbent bed an extract stream containing the adsorbed C$_9$ aromatic isomer. The preferred zeolite beta adsorbent is cation exchanged to increase the C$_9$ aromatic selectivity of the adsorbent.

DETAILED DESCRIPTION OF THE INVENTION

Hydrocarbon feed streams which can be utilized in the process of this invention contain mixtures of C$_9$ aromatic isomers. Specifically, these include the difficult to separate trimethylbenzenes and ethyltoluenes. The ethyltoluene isomers include the ortho, para and meta isomers, while the trimethylbenzene isomers including 1,2,3-trimethylbenzene (hemimellitene), 1,2,4-trimethylbenzene (pseudocumene), and 1,3,5-trimethylbenzene (mesitylene). The close boiling points of these C$_9$ aromatic isomers renders the isomers difficult to separate by distillation. Mixtures containing substantial quantities of C$_9$ aromatic isomers and other aromatics generally are produced by reforming processes, processes which are well known to the refining and petrochemical arts.

The hydrocarbon feed stream is contacted with a bed of the adsorbent, entitled zeolite beta. Zeolite beta and its method of manufacture is described in U.S. Pat. No. 3,308,069 and U.S. Pat. No. Re. 28,341 by Wadlinger et al., this disclosure being fully incorporated herein by reference. Also included within this definition of zeolite beta is where the aluminum is fully or partially substituted with the elements of gallium or boron to provide a gallo silicate or borosilicate or where the silicon is fully or partially substituted with the elements of germanium or phosphorus but retains the same structure and similar x-ray diffraction pattern as defined in the Wadlinger et al. patents. After synthesizing the zeolite beta, it is necessary to calcine the zeolite at a temperature and for a time effective to remove any tetraethylammonium ions remaining after its synthesis. While the zeolite beta composition is fully described in this Wadlinger et al. patent, it has been surprisingly found that zeolite beta can be used to separate C$_9$ aromatic isomers from a feedstream containing a mixture of C$_9$ aromatic isomers. Further, the C$_9$ selectivity can be substantially increased by cation exchanging the zeolite beta with a suitable cation.

The process of this invention may be used to separate all the C$_9$ aromatic isomers from one another by the use of various stages or adsorption zones. The preferred separation is of para-ethyltoluene since it is the most strongly adsorbed C$_9$ aromatic isomer. In general the ethyltoluenes are preferentially adsorbed over the trimethylbenzenes with an order for the decreased preference of adsorption on zeolite beta as follows: p-ethyltoluene > O-ethyltoluene > m-ethyltoluene > p-seudocumene + hemimellitene > mesitylene. In one embodiment of this invention the C$_9$ aromatic isomers are ethyltoluenes which are selectively adsorbed in the order of para-ethyltoluene > ortho-ethyltoluene > meta-ethyltoluene. In another embodiment the C$_9$ aromatic isomers are trimethylbenzenes which are selectively adsorbed in the order of hemimellitene and pseudocumene > mesitylene, with either hemimellitene or pseudocumene being preferentially adsorbed depending upon the particular cation exchanged form of the zeolite beta and the conditions of adsorption.

In order to substantially increase the selectivity of the adsorbent for $C_9$ aromatic isomers, the adsorbent which is available in its tetraethylammonium (TEA)-sodium form is preferably cation exchanged. After the TEA is removed the hydrogen-sodium form of zeolite beta can be exchanged with suitable cations which include base metal or transition metal cations, such as copper, rubidium, nickel, magnesium, strontium, cobalt, potassium, lead, barium, lithium, cadmium, cesium and calcium, or mixtures thereof or other cations, such as ammonium. The preferred cations for increased selectivity are potassium, lithium, cesium, with the most preferred cation being cesium.

The zeolite beta adsorbent can be combined with a binder, such as natural or synthetic clays (e.g. Kaolin), and inorganic oxides and can be in any form acceptable to the separation process such as extrudates, spheres, granules or tablets.

Certain characteristics of adsorbents are highly desirable, if not absolutely necessary, to the successful operation of a selective adsorption process. Among such characteristics are: adsorptive capacity from some weight of the $C_9$ aromatic isomer per weight of adsorbent; and the selective adsorption of a $C_9$ aromatic isomer with respect to a raffinate component and the desorbent material.

Capacity of the adsorbent for adsorbing a specific volume of $C_9$ aromatic isomer is, of course, a necessity; without such capacity the adsorbent is useless for adsorptive separation. Furthermore, the higher the adsorbent's capacity for the $C_9$ aromatic isomer, the better is the adsorbent. Increased capacity of a particular adsorbent makes it possible to reduce the amount of adsorbent needed to separate the $C_9$ aromatic isomer contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. Generally, the adsorbent of this invention has a capacity of at least 3% of hydrocarbon by weight of adsorbent and preferably at least 5% of hydrocarbon by weight of adsorbent.

The second necessary adsorbent characteristic is the ability of the adsorbent to separate components of the feed; or, in other words, that the adsorbent possess adsorptive selectivity, $(\alpha)$, for one component as compared to another component. Relative selectivity can be expressed not only for one feed component as compared to another but can also be expressed between any feed mixture component and the desorbent material. The separation factor, $(\alpha)$, as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (\alpha) = \frac{[\text{weight } C/\text{weight } D]_A}{[\text{weight } C/\text{weight } D]_U}$$

where C and D are two components of the feed represented by weight and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occuring between the unadsorbed and adsorbed phases.

Where selectivity of two components approaches 1.0 there is no preferential adsorption of one component by the adsorbent with respect to ther other; they are both adsorbed (or nonadsorbed) to about the same degree with respect to each other. As the selectivity $(\alpha)$ becomes less than or greater than 1.0 there is preferential adsorption by the adsorbent for one component with respect to the other. When comparing the selectivity by the adsorbent of one component C over component D, at $(\alpha)$ larger than 1.0 indicates preferential adsorption of component C within the adsorbent. An $(\alpha)$ less than 1.0 would indicate that component D is preferentially adsorbed leaving an unadsorbed phase richer in component C and an adsorbed phase richer in component D. For optimum performance desorbent materials should have a selectivity equal to about 1 or less than 1 with respect to all extract components so that all of the extract components can be extracted as a class and all raffinate components clearly rejected into the raffinate stream. When the adsorbent of this invention is cation exchanged it is preferably exchanged with a cation which will impart an $(\alpha)$ separation factor of at least 2.0 of the $C_9$ aromatic isomer (component C) over at least one of the other components (component D) of the hydrocarbon feed stream.

In order to test the various cation exchanged zeolite beta adsorbent materials with a particular feed mixture to measure the characteristics of adsorptive capacity and selectivity, a static testing procedure was employed. The procedure consisted of contacting a known weight of adsorbent with a known weight of mixed hydrocarbon feed stream. After allowing this mixture to reach equilibrium, a sample was removed and analyzed by gas chromatography. The amount of isomers in the raffinate were measured and the amount of isomers adsorbed were obtained by difference from the standard feed stream.

In a separation process, after the hydrocarbon feed stream is contacted with the bed of adsorbent, a raffinate stream is withdrawn from the adsorbent bed, this stream containing less of the selectively adsorbed $C_9$ aromatic isomer of the feed stream. Then the adsorbed aromatic isomer on the bed is desorbed to effect displacement thereof.

The desorbing step which can be used in the various processing schemes employing this adsorbent will vary depending on the type of operation employed. The term "desorbent material" as used herein shall mean any fluid substance capable of removing a selectively adsorbed $C_9$ aromatic isomer from the adsorbent. In the swingbed system in which the selectively adsorbed $C_9$ aromatic isomer is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed $C_9$ aromatic isomer from the adsorbent.

However, in an adsorptive separation process which employs the adsorbent and which is generally operated at substantially constant pressures and temperatures to insure a liquid phase, the desorbent material relied upon must be judiciously selected to satisfy several criteria. First, the desorbent material must displace the $C_9$ aromatic isomer from the adsorbent with reasonable mass flow rates without itself being so strongly adsorbed as to unduly prevent the $C_9$ aromatic isomer from displacing the desorbent material in a following adsorption cycle. Expressed in terms of the selectivity, it is preferred that the adsorbent be more selective for the $C_9$ aromatic isomers with respect to a raffinate (e.g. other isomers), than it is for the desorbent material with respect to a raffinate. Secondly, desorbent materials must be compatible with the particular adsorbent and the particular feed stream. More specifically they must not reduce or destroy the critical selectivity of the adsorbent for the $C_9$ aromatic isomers with respect to the raffinate.

Desorbent materials to be used in the process of this invention should additionally be substances which are easily separable from the feed stream that is passed into the process. After desorbing the $C_9$ aromatic isomer of the feed, both desorbent material and the $C_9$ aromatic isomers are removed in a mixture from the adsorbent. Without a method of separating the desorbent material, such as distillation, the purity of either the $C_9$ aromatic isomer or the raffinate component would not be very high. It is therefore contemplated that any desorbent material used in this process will have a substantially different average boiling point than that of the feed stream. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture.

In a liquid-phase operation of the process of our invention, desorbent materials comprising mono-aromatic hydrocarbons are effective. Mixtures of toluene with paraffins are also effective as desorbent materials. Such paraffins must be compatible with the adsorbent and feed stream as described above and must be easily separated from the feed stream. The paraffins can include straight or branched chain paraffins or cycloparaffins which meet these criteria. Typical concentrations of toluene in such mixtures can be from a few volume percent up to 100 volume % of the total desorbent material mixture but such concentrations preferably will be within the range of from about 50 volume % to about 100 volume % of the mixture. Other desorbents include benzene, diethylbenzene, other polyalkylbenzenes, or more generally polycyclic hydrocarbons etc., and mixtures thereof.

Following desorption, the extract stream containing the $C_9$ aromatic isomer is withdrawn from the adsorbent bed. Depending on the separation factor ($\alpha$) this withdrawn extract can contain relatively pure fractions of $C_9$ aromatic isomer. However, it will be appreciated that the selectively adsorbed component is generally not completely adsorbed by the adsorbent, nor is the raffinate component generally completely non-adsorbed by the adsorbent.

In general, this adsorptive separation process can be carried in the vapor or liquid phase, while the liquid phase is preferable. Adsorption conditions for the process of this invention may include temperatures within the range of from about ambient to about 450° F. (235° C.) and will include pressures in the range from about atmospheric to about 500 psig. Desorption conditions for the process of the invention shall generally include the same range of temperatures and pressures as described for the adsorption operation. The desorption of the selectively adsorbed $C_9$ aromatic isomer could also be effected at subatmospheric pressures or elevated temperatures or both, or by vacuum purging of the adsorbent to remove the adsorbed isomer, but this process is not primarily directed to these desorption methods.

EXAMPLE I

A crystalline aluminosilicate adsorbent zeolite beta having an Al/Si atom ratio of 0.07 in its hydrogen form was cation exchanged with the cations to the extent listed in Table I. A $C_9$ aromatic feedstream containing 0.3% of para-ethyltoluene (PE), 1.15% of meta-ethyltoluene (ME), 0.38% of ortho-ethyltoluene (OE), 1.99% of pseudocumene (PS), 0.55% of mesitylene (MS) and 0.52% of hemimellitene (HE), with the remainder n-hexane, all by weight, was added at ambient temperature to the various cation exchanged zeolite beta adsorbents, with the amount of feedstream being in excess of that which the zeolite can adsorb. After allowing this mixture to reach equilibrium, the mixture was allowed to settle and a sample was removed and analyzed by gas chromatography. The amount of $C_9$ isomers in the raffinate were measured and the amount of isomers adsorbed were obtained by difference from the standard feed stream. The capacity and the ($\alpha$) separation factor were calculated for para-ethyltoluene as compared to the other $C_9$ isomers and between the trimethylbenzene isomers as listed in Table I.

As can be seen from Table I, the potassium and especially the cesium exchanged forms of zeolite beta were highly effective in the separation of para-ethyltoluene from the other $C_9$ aromatic isomers.

EXAMPLE II

A sample of a $C_9$ ethyltoluene aromatic feedstream containing equimolar amounts of para-ethyltoluene (PE), meta-ethyltoluene (ME) and ortho-ethyltoluene (OE) was added to various cation exchanged aluminosilicate zeolite beta adsorbents in an amount equal to the capacity of the adsorbent. After agitation at room temperature to reach equilibrium a gas phase sample was removed and analyzed by gas chromatography. From the peaks of the chromatograms the ($\alpha$) separation factors between the various component of the feedstream were measured. The capacity and ($\alpha$) separation factor are listed on the following Table II.

TABLE II

| | "$\alpha$" Separation Factor | | | |
|---|---|---|---|---|
| Zeolite | PE/ME | PE/OE | OE/ME | Adsorption Capacity wt. % |
| Na—Beta | 2.6 | 2.0 | 1.3 | 23.4 |
| K—Beta | 3.9 | 2.9 | 1.3 | 21.9 |
| Rb—Beta | 4.2 | 2.9 | 1.4 | 22.1 |
| Cs—Beta | 4.3 | 3.5 | 1.2 | 19.9 |

TABLE I

| Cation | HE/PS | PS/MS | HE/MS | OE/ME | "α" Separation Factor PE/HE | PE/MS | PE/PS | PE/ME | PE/OE | % Exchanged |
|---|---|---|---|---|---|---|---|---|---|---|
| H | 0.9 | 5.0 | 4.7 | 1.5 | 2.5 | 11.6 | 2.3 | 2.6 | 1.7 | * |
| Li | 1.3 | 2.2 | 2.8 | 2.1 | 2.5 | 7.1 | 3.2 | 3.3 | 1.6 | 66 |
| K | 1.2 | 2.6 | 3.1 | 3.3 | 10.5 | 32.7 | 12.6 | 7.5 | 2.3 | 41 |
| Cs | 1.5 | 2.1 | 3.2 | 3.0 | 25.2 | 80.5 | 38.9 | 17.0 | 5.7 | 84 |
| Na | 0.9 | 5.0 | 4.7 | 1.5 | 5.7 | 11.6 | 3.9 | 2.6 | 1.7 | 92 |
| Ca | 0.7 | 1.9 | 3.3 | 5.0 | 2.3 | 7.6 | 2.2 | 2.0 | 1.2 | 75 |
| Ba | 1.2 | 3.7 | 6.8 | 1.6 | 7.9 | 34.0 | 9.3 | 4.4 | 0.9 | 65 |
| Co | 0.7 | 2.4 | 4.7 | 2.1 | 2.8 | 12.8 | 3.2 | 3.1 | 1.5 | 82 |
| Mn | 1.0 | 4.7 | 4.8 | 2.4 | 3.1 | 14.7 | 3.1 | 2.7 | 1.1 | 75 |

*In its hydrogen form as synthesized and calcined

EXAMPLE III

A sample of a $C_9$ trimethylbenzene aromatic feedstream containing equimolar amounts of pseudocumene, mesitylene and hemimellitene were added to a Cs aluminosilicate zeolite beta adsorbent as in Example II. The capacity and the α separation factor were calculated for the various components of the feedstream, as listed in Table III.

TABLE III

| "α" Separation Factor | |
|---|---|
| pseudocumene/mesitylene = | 6.9 |
| pseudocumene/hemimellitene = | 2.3 |
| hemimellitene/mesitylene = | 3 |
| Adsorption Capacity Wt. % = | 20.9 |

EXAMPLE IV

A gallosilicate zeolite beta adsorbent was cation exchanged with cations as listed in Table IV. A $C_9$ aromatic feedstream containing 0.3% p-ethyltoluene (PE), 1.0% m-ethyltoluene (ME), 0.3% o-ethyltoluene (OE), 2.0% pseudocumene (PS), 0.5% mesitylene (MS) and 0.5% hemimillitene (HE) with the remainder n-hexane was added to the adsorbent as in Example I. The capacity and the (α) separation factor are calculated as listed in Table IV.

TABLE IV

| Separation Factor | K | Ba | Na | Cs |
|---|---|---|---|---|
| PE/HE | 13.63 | 3.74 | 13.84 | 33.62 |
| OE/ME | 2.64 | 1.92 | 1.46 | 2.33 |
| PE/OE | 1.62 | .60 | 3.17 | 4.46 |
| HE/MS | 4.45 | 2.96 | 2.61 | 4.11 |
| PE/PS | 12.58 | 4.04 | 8.05 | 44.48 |
| OE/PS | 7.79 | 6.73 | 2.54 | 9.97 |
| PE/ME | 4.27 | 1.16 | 4.63 | 10.42 |
| HE/PS | .92 | 1.08 | .58 | 1.32 |
| PS/MS | 4.81 | 2.74 | 4.48 | 3.10 |
| ME/MS | 14.20 | 9.58 | 7.79 | 13.26 |
| ME/PS | 2.95 | 3.50 | 1.74 | 4.27 |
| PE/MS | 60.62 | 11.08 | 36.11 | 138.22 |
| OE/MS | 37.52 | 18.44 | 11.38 | 30.97 |
| Capacity (grams adsorbed per gram of active sieve) | .0483 | .026 | .047 | .044 |

The above examples demonstrate the effectiveness of zeolite beta as an adsorbent for separating $C_9$ aromatic isomers.

What is claimed is:

1. An adsorptive separation process for separating paraethyltoluene from a hydrocarbon feed stream containing a mixture of $C_9$ aromatic isomers comprising:
   (a) contacting said hydrocarbon feed stream with a bed of an adsorbent of zeolite beta;
   (b) withdrawing from said bed of adsorbent a raffinate stream containing less of the selectively adsorbed $C_9$ aromatic isomer of the feed stream;
   (c) desorbing the adsorbed paraethyltoluene to effect displacement thereof; and
   (d) withdrawing from the adsorbent bed an extract stream containing the adsorbed paraethyltoluene.

2. Process of claim 1 wherein the mixture of $C_9$ aromatic isomers are ethyltoluenes which are selectively adsorbed in the order of para-ethyltoluene > ortho-ethyltoluene > meta-ethyltoluene.

3. Process of claim 1 further characterized in that said adsorbent contains at least one cation selected from the group consisting of potassium, barium, rubidium, lithium, sodium and cesium.

4. Process of claim 3 wherein the adsorbent has a cation exchanged with cesium.

5. Process of claim 1 wherein the adsorbed aromatic components are desorbed by passing a desorbent material through said bed.

6. Process of claim 1 further characterized in that said adsorbent contains at least one cation which imparts an (α) separation factor of at least 2.0 of the adsorbed aromatic isomer over at least one of the other components of the hydrocarbon feed stream.

7. Process of claim 5 wherein the desorbent is selected from the group consisting of toluene, benzene, paraffin, diethylbenzene, alkyl benzene, polycyclic hydrocarbons and mixtures thereof.

8. Process of claim 1 wherein the zeolite beta adsorbent comprises a silicate chosen from the group consisting of aluminosilicate, borosilicate and gallosilicate.

9. Process of claim 8 wherein the silicon is fully or partially substituted with an element chosen from the group consisting of germanium and phosphorus.

10. Process of claim 1 wherein the zeolite beta adsorbent is an aluminosilicate.

11. Process of claim 1 wherein the separation is carried out at a temperature within the range of ambient to 450° F. and a pressure within the range of atmospheric to 500 psig.

12. Process of claim 1 wherein the process is carried out in the liquid phase.

13. Process of claim 1 wherein the process is carried out in the vapor phase.

14. Process of claim 1 wherein the adsorbent is combined with a binder.

15. Process of claim 13 wherein the binder is selected from the group consisting of natural and synthetic clays and inorganic oxides.

16. Process of claim 1 further characterized in that said adsorbent has a capacity of at least 3% of hydrocarbon by weight of adsorbent.

17. An adsorptive separation process for separating at least one $C_9$ aromatic isomer from a hydrocarbon feed stream containing a mixture of $C_9$ aromatic isomers, wherein the mixture of $C_9$ aromatic isomers contain trimethylbenzenes which are selectively adsorbed in the order of pseudocumene and hemimellitene > mesitylene, comprising:
  (a) contacting said hydrocarbon feed stream with a bed of adsorbent of zeolite beta;
  (b) withdrawing from said bed of adsorbent a raffinate stream containing less of the selectively adsorbed $C_9$ aromatic isomer of the feed stream;
  (c) desorbing the adsorbed $C_9$ aromatic isomer to effect displacement thereof; and
  (d) withdrawing from the adsorbent bed an extract stream containing the adsorbed $C_9$ aromatic isomer.

18. Process of claim 17 further characterized in that said adsorbent contains at least one cation selected from the group consisting of potassium, barium, rubidium, lithium, sodium and cesium.

19. Process of claim 18 wherein the adsorbent has a cation exchanged with cesium.

20. Process of claim 17 wherein the adsorbed aromatic components are desorbed by passing a desorbent material through said bed.

21. Process of claim 17 further characterized in that said adsorbent contains at least one cation which imparts an ($\alpha$) separation factor of at least 2.0 of the adsorbed aromatic isomer over at least one of the other components of the hydrocarbon feed stream.

22. Process of claim 20 wherein the desorbent is selected from the group consisting of toluene, benzene, paraffin, diethylbenzene, alkyl benzene, polycyclic hydrocarbons and mixtures thereof.

23. Process of claim 17 wherein the zeolite beta adsorbent comprises a silicate chosen from the group consisting of aluminosilicate, borosilicate and gallosilicate.

24. Process of claim 23 wherein the silicon is fully or partially substituted with an element chosen from the group consisting of germanium and phosphorus.

25. Process of claim 17 wherein the zeolite beta adsorbent is an aluminosilicate.

26. Process of claim 17 wherein the separation is carried out at a temperature within the range of ambient to 450° F. and a pressure within the range of atmospheric to 500 psig.

27. Process of claim 17 wherein the process is carried out in the liquid phase.

28. Process of claim 17 wherein the process is carried out in the vapor phase.

29. Process of claim 17 wherein the adsorbent is combined with a binder.

30. Process of claim 28 wherein the binder is selected from the group consisting of natural and synthetic clays and inorganic oxides.

31. Process of claim 17 further characterized in that said adsorbent has a capacity of at least 3% of hydrocarbon by weight of adsorbent.

* * * * *